United States Patent
Tompers et al.

(10) Patent No.: US 9,744,525 B2
(45) Date of Patent: Aug. 29, 2017

(54) CATALYST FOR THE OXYCHLORINATION OF ETHYLENE TO 1, 2-DICHLOROETHANE

(71) Applicant: BASF Corporation, Florham Park, NJ (US)

(72) Inventors: Rolf Tompers, Mannheim (DE); Keith Kramer, Andover, KS (US)

(73) Assignee: BASF CORPORATION, Florham Park, NJ (US)

( * ) Notice: Subject to any disclaimer, the term of this patent is extended or adjusted under 35 U.S.C. 154(b) by 0 days.

(21) Appl. No.: 14/996,474

(22) Filed: Jan. 15, 2016

(65) Prior Publication Data

US 2016/0129426 A1 May 12, 2016

Related U.S. Application Data

(63) Continuation of application No. 14/072,057, filed on Nov. 5, 2013, now Pat. No. 9,248,434.

(60) Provisional application No. 61/723,009, filed on Nov. 6, 2012.

(51) Int. Cl.
| | | |
|---|---|---|
| *B01J 23/88* | (2006.01) | |
| *C07C 17/156* | (2006.01) | |
| *B01J 37/08* | (2006.01) | |
| *B01J 35/10* | (2006.01) | |
| *B01J 37/02* | (2006.01) | |
| *B01J 23/889* | (2006.01) | |
| *B01J 35/02* | (2006.01) | |
| *B01J 21/04* | (2006.01) | |

(52) U.S. Cl.
CPC ....... *B01J 23/8892* (2013.01); *B01J 35/1014* (2013.01); *B01J 35/1019* (2013.01); *B01J 37/0201* (2013.01); *B01J 37/0236* (2013.01); *B01J 37/08* (2013.01); *C07C 17/156* (2013.01); *B01J 21/04* (2013.01); *B01J 23/8896* (2013.01); *B01J 35/023* (2013.01)

(58) Field of Classification Search
CPC .... B01J 23/8892; B01J 23/8896; B01J 37/08; B01J 37/0201; B01J 35/1019; B01J 35/1014; B01J 35/023; B01J 21/04; B01J 23/72; B01J 23/78; B01J 23/84; C07C 17/156
See application file for complete search history.

(56) References Cited

U.S. PATENT DOCUMENTS

| | | |
|---|---|---|
| 4,460,699 A | 7/1984 | Convers |
| 4,754,088 A | 6/1988 | Schmidhammer et al. |
| 5,382,726 A | 1/1995 | Young et al. |
| 2007/0112235 A1 | 5/2007 | Kramer et al. |
| 2010/0274061 A1 | 10/2010 | Urtel et al. |

FOREIGN PATENT DOCUMENTS

| | | |
|---|---|---|
| DE | 90127 | 5/1972 |
| EP | 0582165 B1 | 5/1993 |
| EP | 0375202 B1 | 9/1993 |
| EP | 1464395 | 10/2004 |
| GB | 1223804 | 3/1971 |
| RU | 2148432 C1 | 5/2000 |

OTHER PUBLICATIONS

International Preliminary Report on Patentability on application No. PCT/US2013/068705, mailed on May 12, 2015.
International Preliminary Report on Patentability dated May 21, 2015.
Supplementary European Search Report for EP Application No. 13851413.8, dated Jul. 4, 2016, 2 pages.

*Primary Examiner* — Anthony J Zimmer
(74) *Attorney, Agent, or Firm* — Lowenstein Sandler LLP

(57) ABSTRACT

This invention relates to a catalyst containing from about 2 up to about 8% by wt. of copper, zero up to about 0.6 moles/kg of one or more alkali metal(s), from about 0.08 up about 0.85 moles/kg of one or more alkaline earth metals and from about 0.09 up to about 0.9 moles/kg of one or more transition metals selected from the group consisting of Mn, Re and mixtures thereof, where all the metals are impregnated in form of their chlorides or other water soluble salts on a fluidizable support with a BET surface area of from about 80 up to about 220 m$^2$/g. A process for the oxychlorination of ethylene to form 1,2-dichloroethane using such a catalyst having good activity, good selectivity and low tendency to stickiness in fluidized bed oxychlorination reactions.

16 Claims, No Drawings

CATALYST FOR THE OXYCHLORINATION OF ETHYLENE TO 1, 2-DICHLOROETHANE

CROSS REFERENCE TO RELATED APPLICATIONS

This application is a continuation of U.S. patent application Ser. No. 14/072,057, filed on Nov. 5, 2013, claiming priority of U.S. Provisional Application No. 61/723,009, filed Nov. 6, 2012, which are hereby incorporated by reference in their entirety.

TECHNICAL FIELD

The present invention relates to a catalyst and a process for using said catalyst for the oxychlorination of ethylene with HCl and oxygen (or an oxygen containing gas) to form 1,2-dichloroethane.

BACKGROUND

EP0375202 describes an oxychlorination catalyst composition comprising a mixture of metallic chlorides carried on a support, wherein said mixture consists essentially of a mixture of copper chloride, magnesium chloride, and potassium chloride. It also describes the oxychlorination of ethylene to 1,2-dichloroethane using such a catalyst composition.

DD 90127 relates to a method for producing 1,2-dichloroethane by oxychlorination of ethylene with hydrogen chloride and air. As catalysts according to the invention, mixtures are used which contain copper (II)-chloride as the principal component and as promoters contain chlorides of the metals silver, magnesium, calcium, potassium, cerium and manganese, applied to an inert support. The catalysts are composed of 6 to 10 wt. % of the active catalyst components and 94 to 90 wt. % of the inert support.

RU 2148432 relates to catalytic chemistry and in particular to catalysts for the synthesis of dichloroethane by oxychlorination of ethylene. The method described for preparation of a catalyst for oxychlorination of ethylene to 1,2-dichloroethane includes application of a copper compound as an active component to an aluminum oxide carrier containing a metal ion $Me^{2+}$ and/or $Me^{3+}$ in the aluminum oxide with a ratio of $Al^{3+}$ to $Me^{2\pm}$ and/or $Me^{3+}$ in the range from 200:1 to 20:1, with subsequent drying at a temperature ensuring complete crystallization of the active component over a period of less than 30 min. Application of the active component to the carrier and drying are carried out in a controlled-speed rotary drum fitted with a device for introducing an impregnating solution and a heating element for performing the drying.

EP 0582165 relates to catalyst compositions for oxychlorination of ethylene to produce 1,2-dichloroethane. The catalysts comprise copper chloride, at least one alkali metal, at least one rare earth metal, and at least one Group IIA metal on a high surface area support for fluid bed applications or on a high or low surface area support for fixed bed applications. The catalyst compositions are prepared by depositing the metals on a support. The use of the catalyst compositions of the invention in the oxychlorination of ethylene to EDC results in high percent ethylene efficiency, high EDC product purity and high percent HCl conversion without exhibiting catalyst stickiness. A process for oxychlorination of ethylene to produce 1,2-dichloroethane is also disclosed. The process relies on contacting a mixture of ethylene, oxygen or oxygen containing gas and hydrogen chloride with a fixed or fluidized catalyst composition in a reaction zone and recovering 1,2-dichloroethane from the effluents of the reaction zone.

The most commonly used process for the production of 1,2-dichloroethane is the oxychlorination of ethylene. In this process ethylene is converted with HCl and oxygen (or an oxygen containing gas) to form 1,2-dichloroethane and water. In the course of the years both fixed and fluidized bed process variants have been developed and are currently in use.

The by-products formed in the oxychlorination process are carbon oxides ($CO+CO_2$) and chlorinated hydrocarbons. Among these chlorinated by-products 1,1,2-trichloroethane, chloral, ethylchloride, chloroform and carbon tetrachloride are the most common. All by-products lead to a loss in ethylene efficiency and have to be minimized. The chlorinated by-products also need to be incinerated and hence produce further costs.

The catalysts used in oxychlorination processes contain copper chloride as an active ingredient. In order to improve the activity, selectivity and/or the operability, further promoters are introduced into the catalyst formulation. Among the most commonly used are magnesium chloride, potassium chloride, cesium chloride and/or rare earth chlorides.

The active copper species as well as the promoters are usually deposited on a high surface support like kieselguhr, clay, fuller's earth, silica or alumina. In general the copper and the promoters are impregnated onto the support by means of a solution containing all the metals in form of their chlorides. In some cases a co-precipitation of the ingredients with the support is carried out.

In the meantime fluidized bed oxychlorination processes became favored over fixed bed processes due to better economics. Commercial fluidized bed reactors are usually operated with an HCl conversion of 99.5 to 99.8%. The 1,2-dichloroethane selectivity typically lies between 96-97.5%.

The supports used for the production of fluidized bed oxychlorination catalysts are mostly fluidizable gamma alumina with a mean particle size of 30-80 µm and a BET surface area of 120-220 $m^2/g$.

The copper content of fluidized bed oxychlorination catalysts typically lies between 3-17 wt. %. Most fluidized bed processes use catalysts with a copper content of 3-6 wt. %.

In fluidized bed oxychlorination a phenomenon called "catalyst sticking" or "stickiness" can occur under certain conditions. "Sticky Catalyst" results in the agglomeration of catalyst particles resulting often in the collapse of the fluidized bed and/or the plugging of the cyclones. As a consequence severe catalyst carry-over can take place and the reactor is no longer operable. Such a sticking episode causes significant economic damage to a production plant and has to be avoided by all means. Stickiness in oxychlorination can be caused either by inappropriate operational conditions or by the properties of the catalyst itself. The following operational conditions favor stickiness:
  i) high Cl/C ratio
  ii) low O/C ratio
  HO low operation temperature.
Hence a fluidized bed oxychlorination catalyst must have a high resistance towards stickiness.

SUMMARY OF THE INVENTION

One aspect is directed to a catalyst for the oxychlorination of ethylene to form 1,2-dichloroethane. Various embodiments are listed below. It will be understood that the embodiments listed below may be combined not only as listed below, but in other suitable combinations in accordance with the scope of the invention.

In embodiment one, the catalyst comprises: from about 2 up to about 8% by wt. of copper, zero up to about 0.6 moles/kg of one or more alkali metals, from about 0.08 up to about 0.85 moles/kg of one or more alkaline earth metals and from about 0.09 up to about 0.9 moles/kg of one or more transition metals selected from the group consisting of Mn, Re or mixtures thereof, where all the metals are impregnated in form of their chlorides or other water soluble salts on a fluidizable support with a BET surface area of from about 80 up to about 220 $m^2/g$.

Embodiment two includes a more specific catalyst comprising: from about 2 up to about 8% by wt. of copper, zero up to about 2% by wt. of potassium, from about 0.2 up about 2.0% by wt. of magnesium and from about 0.5 up to about 5.0% by wt. of manganese, where all the metals are impregnated in form of their chlorides or other water soluble salts on a fluidizable support with a BET surface area of from about 80 up to about 220 $m^2/g$.

Embodiment three includes a process for the oxychlorination of ethylene to form 1,2-dichloroethane.

Embodiment four provides an oxychlorination catalyst having good activity, good selectivity and low tendency to stickiness in fluidized bed oxychlorination reactions.

Embodiment five provides a more specific elemental composition of the catalyst according to the invention is from about 3 up to 6% by wt. of copper, zero up to about 1.3% by wt. of potassium, from about 0.8 up to about 1.5% by wt. of magnesium and from about 0.5 up to about 2.0% by wt. of manganese, the remainder being chlorides and alumina.

Embodiment six provides that the amount of potassium that is put on the catalyst regulates the operation temperature of the catalyst as well as the by-product composition.

Embodiment seven provides that catalysts of this invention with no or little potassium show a higher HCl conversion and a better EDC crude purity at lower temperature.

Embodiment eight provides catalysts of this invention with higher amounts of potassium show a somewhat lower crude purity but can therefore be operated at higher temperatures without producing too much carbon oxides.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

The catalyst compositions of this invention employ support materials which are readily available. For fluid bed catalysis, the metals should be deposited on high surface area supports. The principle reason for the requirement of high surface area supports in fluid bed catalysis is the necessity to reduce the stickiness of the catalyst as the metal can be dispersed over a large area. Examples of support materials include but are not limited to materials such as silica, magnesia, kieselguhr, clay, fuller's earth, alumina or combinations thereof. The preferred catalytic process is fluid bed catalysis using a high surface area support.

Examples of fluidizable high surface area supports include but are not limited to materials such as silica, magnesia, kieselguhr, clay, fuller's earth, alumina or combinations thereof. The preferred supports are high surface area aluminas (often referred to as gamma, delta or theta-alumina). The preferred supports are activated or transition aluminas generated by calcination of a hydrated or hydroxylated precursor alumina. These activated aluminas can be identified by their disordered structures observable by their X-ray diffraction patterns that indicate a mixed phase material containing minimal to no low surface area or crystalline phase alpha alumina. Alpha alumina is identified by a defined crystalline phase by x-ray diffraction. The higher surface area activated aluminas are often defined as a gamma alumina phase but in reality the phase transitions are a continuum of varying percentages of multiple mixed phases such as, but not limited, to delta and theta phases based on the chosen calcination temperature to achieve the desired support surface area. Alumina supports having a surface area greater than 80 $m^2/g$ are preferred in order to properly disperse the metal load and help to prevent tendency toward stickiness. The invention will be described hereinafter in terms of alumina supports. This is meant to be illustrative and not limiting. The fluidizable alumina support material has a surface area in the range of about 80 to 220 $m^2/g$, more specifically 100 to 220 $m^2/g$ and even more specifically 120-220 $m^2/g$, a compacted bulk density in the range of 0.7 to 1.3 $g/cm^3$, a pore volume in the range of 0.2 to about 1 $cm^3/g$ and a particle size distribution such that about 90 to 100 percent by volume of the particles are below 150 microns in diameter. Such alumina support materials are readily fluidizable, relatively stable, mechanically strong and resistant to attrition. Aluminas particularly useful for the purposes of this invention are Sasol products Puralox® and Catalox® high purity activated aluminas.

Additionally, the alumina supports can be stabilized by any means in the art to prevent undesirable changes in the activated alumina phase once the finished catalyst is in service. Examples of such stabilizing components include but are not limited to the inclusion of La, Ce, Ti, Si, etc. as trace components dispersed throughout the alumina support prior to impregnation of the active catalyst formulation.

It is recognized that some alumina support materials may contain in addition to aluminum oxide ($Al_2O_3$) and stabilizing components small amounts of impurities of other metals such as metal oxides like up to 0.02 wt. % of sodium oxide, up to 0.05 wt. % of iron oxide ($Fe_2O_3$), up to 0.3 wt.

% of titanium dioxide, up to 0.2 wt. % of silicon dioxide, etc. These alumina supports are readily useable in this invention.

It was discovered that only particular ranges of loadings of copper, alkali metal(s), alkaline earth metal(s) and one or more transition metals selected from the group selected from Mn and Re, will result in all of the high performance characteristics described above. Outside of the particular loadings of the active metals, high performance in all respects is not achieved.

The copper compound is used in the form of a water soluble salt, and preferably is used in the form of copper chloride. However, other copper salts that could convert to the chloride during the oxychlorination process can also be used, such as the nitrate salt, carbonate salt or other halide salts like the bromide salt. The copper salt is deposited on the alumina support using the same techniques as described above. The amount of copper metal deposited is based on the activity desired and the specific fluidization characteristics of the support for fluid bed catalyst applications. The amount of copper metal employed is in the range from about 2% by weight to about 8% by weight as copper metal based on the total weight of the catalyst composition. The preferred copper salt is copper chloride. The preferred minimum amount of copper metal is from about 2.0% by weight based on the total weight of the catalyst. A more specific minimum amount of copper metal is about 3.0% by weight based on the total weight of the catalyst. A preferred maximum amount of copper metal is about 8.0% by weight based on the total weight of the catalyst. A more specific maximum amount of copper metal is about 6.0% by weight based on the total weight of the catalyst. The final catalyst composition containing the alkali metal(s), alkaline earth metals(s), one or more transition metals selected from the group selected from Mn and Re and copper compound is readily fluidizable.

The alkali metals employed in the present invention can be sodium, potassium, lithium, rubidium, or cesium, or a mixture of one or more such metals. The alkali metal is used in the form of a water soluble salt, and preferably is used in the form of an alkali metal chloride. However, other alkali metal salts that would convert to the chloride salt during the oxychlorination process can also be used, such as the nitrate salt, the carbonate salt or other halide salts like the bromide salts. The alkali metal is used in the range from zero up to about 0.6 moles/kg, more specifically up to about 0.4 moles/kg and even more specifically from about 0.1 up to about 0.4 moles/kg (as the metal) based on the total weight of the catalyst composition. The preferred alkali metals are potassium, lithium, and cesium. The most preferred alkali metal is potassium, and the preferred alkali metal salt is potassium chloride. The amount of potassium that is put on the catalyst regulates the operation temperature of the catalyst as well as the by-product composition. Catalysts of this invention with little or no potassium show a higher HCl conversion and a better EDC crude purity at lower temperature. Higher amounts of potassium show a somewhat lower crude purity but can be operated at higher temperatures without producing too much carbon oxides A preferred maximum amount of alkali metal is about 0.6 moles/kg based on the total weight of the catalyst. A more preferred maximum amount of alkali metal is about 0.4 moles/kg based on the total weight of the catalyst.

Alkaline earth metals employed in the present invention can be magnesium, calcium, strontium, or barium, or a mixture of one or more such metals. The alkaline earth metals are used in the form of a water soluble salt, and preferably are used in the form of an alkaline earth metal chloride. However, other alkaline earth metal salts that would convert to the chloride salt during the oxychlorination process can also be used, such as the nitrate salt, the carbonate salt or other halide salts like the bromide salts. The alkaline earth metals are used in the range from about 0.08 up about 0.85 moles/kg, more specifically from 0.2 up to about 0.75 moles/kg and even more specifically from about 0.3 up to about 0.62 moles/kg (as the metal) based on the total weight of the catalyst composition. The preferred alkaline earth metals are magnesium, calcium and barium. The most preferred alkaline earth metal is magnesium, and the preferred alkaline earth metal salt is magnesium chloride.

A preferred maximum amount of alkaline earth metal is about 0.85 moles/kg based on the total weight of the catalyst. A more specific maximum amount of alkaline earth metal is about 0.75 moles/kg and even more specifically from about 0.62 moles/kg based on the total weight of the catalyst.

Transition metals employed in the present invention are Mn, Re, or mixtures of such metals. These transition metals are used in the form of a water soluble salt, and preferably are used in the form of a manganese or rhenium chloride. However, other Mn or Re salts that would convert to the chloride salt during the oxychlorination process can also be used, such as the nitrate salt, the carbonate salt or other halide salts like the bromide salts. These transition metals are used in the range from 0.09 up to about 0.9 moles/kg, more specifically from 0.09 up to about 0.4 moles/kg and even more specifically up to about 0.28 moles/kg (as the metal) based on the total weight of the catalyst composition. The preferred transition metal is manganese, and the preferred transition metal salt is manganese chloride.

A preferred maximum amount of transition metal is about 0.9 moles/kg, based on the total weight of the catalyst. A more specific maximum amount of transition metal is 0.4 moles/kg and even more specifically is about 0.28 moles/kg based on the total weight of the catalyst.

Other metals can be present in the catalyst compositions of the invention in relatively small amounts. For example, rare earth metals and/or transition metals other than manganese and rhenium. Typically, these metals, if present, may be present in amounts up to about 2.75 moles/kg based on the total weight of the catalyst composition. Other transition metals that may be present in this invention include Fe, Nb, Mo, Co, V, W, Ni, Cr, and precious metals such as Au, Ru and Pd.

The rare earth metals that may be employed in the invention can be any of the elements listed as elements 57 through 71 of the Periodic Table and the pseudo rare earth elements yttrium and scandium. Examples of rare earth metals include lanthanum, cerium, praseodymium, neodymium, or naturally occurring mixtures of one or more such metals such as didymium. The rare earth metal is used in the form of a rare earth metal chloride. However, other rare earth metal salts which would convert to the chloride during the oxychlorination process can also be used, e.g., carbonate salts, nitrate salts or other halide salts like a bromide salt. For reasons of the high cost of rare earth metals, it is preferred to have little or no rare earths present in the catalyst.

One method of addition of the metals onto the alumina support is accomplished by impregnating the support with an aqueous solution of a water soluble salt of the metals along with a water soluble salt of the copper compound and then drying the wetted support. The alkali metal(s), alkaline earth metal(s), one or more transition metals selected from the group consisting of Mn and Re and any additional metals could be but do not have to be calcined on the support prior to deposition of the copper compound to produce a fluidizable catalyst.

The specific characteristics such as surface area and pore volume, for example, are, of course, modified by reason of the deposit of the metal salts. Hence, the catalyst compositions of this invention have a final surface area in the range of about 20 to about 220 m$^2$/g. The preferred range of surface areas for fluid bed catalysts is about 60 to about 180 m$^2$/g. The most preferred range of surface area for fluid bed catalysts is from about 80 to about 160 m$^2$/g.

The catalyst compositions of this invention are readily prepared by wetting the alumina support material, as above described, with an aqueous solution of salts of the desired metals. The wetted alumina is then dried slowly at about 80° C. to 240° C. to remove water. An amount of the metal salt is chosen so that the final catalyst contains from about 2% to about 8% by weight of copper, zero to about 0.6 moles/kg of the incorporated alkali metal(s) and from about 0.08% to about 0.85 moles/kg of alkaline earth metal(s), and from about 0.09 to about 0.9 moles/kg of one or more transition metals selected from the group consisting of Mn and Re, all metals based on the total weight of the catalyst composition. The metal salt used in the aqueous solution can be in the form of any water soluble salt such as previously described, like the chloride or carbonate salt. The subject invention also contemplates a process for oxychlorination of ethylene to form ethylene dichloride (EDC). The process comprises contacting ethylene, oxygen or an oxygen containing gas and hydrogen chloride (HCl) with a catalyst composition in a reaction zone and recovering the effluent of the reaction zone. The catalyst employed comprises copper, alkali metal(s), alkaline earth metal(s) and one or more transition metals selected from the group consisting of Mn, Re and mixtures thereof. The metals are deposited on a high surface area support for fluid bed applications.

This process can be carried out as a once through process wherein any unreacted ethylene is vented or otherwise removed, or in a recycle process wherein the unreacted ethylene is recycled back into the reactor. In the recycle process the ratio of HCl to ethylene will tend to be lower at a molar ratio of about 1 to about 2.

The catalyst compositions of the invention are highly efficient catalysts for the oxychlorination of ethylene to EDC. The reaction process temperatures vary from about 180° C. to about 260° C., and more specifically from about 210° C. to 250° C. Reaction pressures vary from atmospheric to as high as about 200 psig. Contact times in the fluid bed and fixed bed catalysis can vary from about 10 seconds to about 50 seconds (contact time is defined here as the ratio of reactor volume taken up by the catalyst to the volumetric flow rate of the feed gases at the reactor control temperature and top pressure), and more preferably are from about 20 to 35 seconds. The ratio of the ethylene, HCl, and oxygen reactants, based on the moles of HCl fed to the reactor, range from about 1.0 to about 2.0 moles of ethylene and about 0.5 to about 0.9 mole of oxygen per 2.0 moles of HCl. As previously mentioned, modern oxychlorination processes attempt to operate within the stoichiometric ratio of about 1 to about 2 moles of HCl to 1 mole of ethylene.

The specific Examples set forth below illustrate the unique and unexpected characteristics of the catalyst compositions of this invention, and are not intended to be limiting of the invention. The Examples particularly point out the criticality of using a combination of copper chloride, alkali metal(s), alkaline earth metals and one or more transition metals selected from the group consisting of Mn, Re and mixtures thereof. In all of the Examples, the fluid bed oxychlorination reaction is conducted using a laboratory scale fluid bed reactor. The reactor volume, the amount of catalyst charged to the reactor, the fluid density, the reactant flow rates, the temperature and the pressure all affect the contact time between reactants and catalyst. Reactor height to diameter ratio can also effect reaction conversions, selectivities, and efficiencies. Therefore, in order to insure that measured differences in catalyst performance results are due strictly to inherent differences in catalyst characteristics rather than to differences in reactor geometry or reactor conditions, all catalyst performance evaluations are conducted in virtually identical laboratory scale reactors using the same reaction contact time, the same set of feed conditions, and the same reactor control methods. The reactor is equipped with means for delivering gaseous ethylene, oxygen, nitrogen, and HCl through the reactor zone, means for controlling the quantities of reactants and reaction conditions, and means for measuring and ascertaining the composition of the effluent gases to determine the percent HCl conversion, percent yield of EDC, and percent ethylene efficiency and EDC product purity. The results provided in the examples below are calculated as follows:

$$\text{HCl conversion}(\%) = \frac{\text{mol HCl converted in the reactor}}{\text{mol HCl fed to the reactor}} \times 100$$

$$\text{ethylene conversion}(\%) = \frac{\text{mol ethylene converted in the reactor}}{\text{mol ethylene fed to the reactor}} \times 100$$

$$\text{EDC selectivity}(\%) = \frac{\text{mol ethylene converted to 1, 2-dichloroethane}}{\text{mol ethylene converted in total}} \times 100$$

$$\text{CO}_X \text{ selectivity}(\%) = \frac{\text{mol of ethylene converted in CO}_X}{\text{mol of ethylene converted in total}} \times 100$$

$$\text{Cl-by-product selectivity}(\%) = \frac{\text{mol of ethylene converted to chlorinated by-products}}{\text{mol of ethylene converted in total}} \times 100$$

$$\text{EDC crude purity}(wt. \%) = \frac{\text{Mass of 1, 2-dichloroethane formed}}{\text{Mass of total chlorinated organic compounds formed}} \times 100.$$

EXAMPLES

Testing in Reactor 1

Test reactor 1 is a tubular glass reactor with an internal diameter of 2 cm. The reactor is operated at atmospheric pressure and is filled with an amount of catalyst leading to a fluidised bed height of 99±2.5 cm. The feed gas is composed of 11.4 NL/h of N$_2$, 3.75 NL/h of ethylene, 7.12 NL/h of HCl and 2.55 NL/h of O$_2$. The reaction temperature is measured with a centered thermocouple in the fluidized bed and regulated on behalf of external electric heating. The reaction temperature range can be widely varied and typically lies between 205 and 230° C. HCl in the feed and in the product gas is measured via titration. N$_2$, C$_2$H$_2$, O$_2$, CO$_x$ and chlorinated hydrocarbons are measured via GC (HP 6890 Series; Column types—1) Vocol glass capillary column (60 meter; 0.75 mm ID; 1.5 micron film thickness. 2) 80/100 Porapak N column (12 foot×⅛ inch, stainless steel). 3) 60/80 molecular sieve, 5 angstrom (6 foot×⅛ inch); Detectors—2 TCD's. Detector B (Vocal column) Detector A (mol sieve/Porapak); One TCD is used to detect light gases, such as $O_2$, $N_2$, and CO from the molecular sieve column, and heavier gases, such as $CO_2$ and ethylene as well as lighter chlorinated hydrocarbons such as vinyl chloride and ethyl chloride from the Porapak column. The second TCD is used to detect the remaining heavier chlorinated hydrocarbons from the Vocol column starting with chloroform, including EDC and other heavier chlorinated by-products.).

Based on the analytics and the feed gas amounts, the HCl conversion, the ethylene conversion, the EDC selectivity and the selectivity of the different oxidised and chlorinated by-products could be calculated. The chemical performance is evaluated at temperatures above 210° C. where the HCl conversion is higher than 98%. The sticking resistance is evaluated by gradually lowering the temperature to the point where visual agglomerations of the catalyst, fluctuations in the differential pressure or sudden changes in selectivity occur. More specifically, the observation of catalyst stickiness is achieved both visually and by measuring the change in the pressure drop across the fluidized bed using a differential pressure metering device. Under typical fluidization or non-sticky conditions the catalyst is moving freely and smoothly in the reactor with a fairly constant effluent gas exit rate where gaseous pockets or bubbles observed within the bed are of small diameter and minimal in quantity. This visual observation corresponds to a measured differential pressure that contains very little noise or fluctuation in the differential pressure value that is observed during good fluidization or non-sticky conditions. As the catalyst becomes sticky the fluid-bed height can increase by up to 10% of the normal bed height prior to fluidization failure or the onset of severe catalyst stickiness. At the failure point slugging of the catalyst bed is observed where large gas pockets are formed and the catalyst is no longer fluidizing well but instead is showing particle clustering or agglomeration. Additionally, the pressure differential observed across the fluid-bed becomes unstable resulting in larger than normal swings relative to when operating under non-sticky conditions. A typical differential pressure reading of 85 mbar can vary by +/−1 mbar under non-sticky operating conditions. This "low noise" pressure reading relates to good fluidization or non-sticky operating conditions. When the differential pressure reading consistently varies by more than +/−3 mbar this "high noise" condition represents the point of poor fluidization or catalyst stickiness.

All the catalysts are tested under the same conditions in reactor 1 so that a direct comparison of the results is ensured.

Testing in Reactor 2

Test reactor 2 is a tubular glass reactor with an internal diameter of 2 cm. The reactor is operated at 4 bar and is filled with an amount of catalyst leading to a fluidized bed height of 114±2 cm. The feed gas is composed of 45.5 NL/h of $N_2$, 14.95 NL/h of ethylene, 28.40 NL/h of HCl and 10.16 NL/h of $O_2$. The reaction temperature is measured with a centered thermocouple in the fluidized bed and regulated by oil heating. The reaction temperature range lies between 210 and 240° C. HCl in the feed and in the product gas is measured via titration. $N_2$, $C_2H_2$, $O_2$, $CO_x$ and chlorinated hydrocarbons are measured via GC—an Agilent 6890N equipped with two columns. One column (DB-123-1063) is connected to an FID and used to measure ethylene and the chlorinated hydrocarbons. The other column (Varion CP 7430) is connected to a TCD and used to measure $O_2$, $N_2$, CO and $CO_2$. Based on the analytics and the feed gas amounts, the HCl conversion, the ethylene conversion, the EDC selectivity and the selectivity of the different oxidised and chlorinated by-products is calculated. The chemical performance is evaluated at temperatures above 220° C. where the HCl conversion is higher than 98%. The sticking resistance is evaluated by gradually lowering the temperature to the point where visual agglomerations of the catalyst, fluctuations in the differential pressure or sudden changes in selectivity occur.

All the catalysts are tested under the same conditions in reactor 2 so that a direct comparison of the results is ensured.

Preparation of the Catalysts

The catalysts are prepared by impregnating an alumina purchased from an external supplier with an aqueous solution of the desired metals. The volume of the solution corresponded to 95-115% of the pore volume of the support. The metal salts used are $CuCl_2.2H_2O$, KCl, $MgCl_2.6H_2O$, $MnCl_2.4H_2O$, $LaCl_3.7H_2O$, $CeCl_3.7H_2O$, $PrCl_3.6H_2O$. The impregnation is carried out at room temperature in a rotary drum equipped with a spray nozzle. Subsequent to the impregnation the catalyst is first pre-dried for four hours in a rotary drum, then it is further dried in a cabinet dryer according to the following temperature profile: 16 h at 110° C., 2 h at 130° C., 2 h at 150° C., 4 h at 180° C.

Example 1a (According to the Invention)

The metal chlorides are impregnated on an alumina support from Sasol with the labelling Catalox SCCa 25/200 (This support has a pore volume of 0.43 mL/g and a surface area of 200 m$^2$/g. The psd of the alumina is such that 1.6% of the particles is smaller than 22 μm, 8.8% of the particles is smaller than 31 μm, 28.5% of the particles is smaller than 44 μm, 84.7% of the particles is smaller than 88 μm and 98.1% of the particles is smaller than 125 μm.). The metal composition is 4.3 wt. % Cu, 1.3 wt. % Mg, 1.1 wt. % K, 1.0 wt. % Mn.

Example 1b (According to the Invention)

The metal chlorides are impregnated on an alumina support from Sasol with the labelling Puralox SCCa 25/200 (This support has a pore volume of 0.45 mL/g and a surface area of 200 m$^2$/g. The psd of the alumina is such that 0.7% of the particles is smaller than 22 μm, 5.7% of the particles is smaller than 31 μm, 25.1% of the particles is smaller than 44 μm, 85.8% of the particles is smaller than 88 μm and 98.5% of the particles is smaller than 125 μm). The metal composition is 4.3 wt. % Cu, 1.3 wt. % Mg, 1.1 wt. % K, 1.0 wt. % Mn Example 1c (According to the Invention)

Example 1c corresponds to Example 1a in terms of raw materials and chemical composition. The impregnation is carried out in a V-blender at 60-75° C., the volume of the impregnation solution is 90%±5% of the pore volume of the alumina support. The drying is carried out in a dryer that was operated between 100-140° C. The example is mentioned to show that the conditions of impregnation and drying can be varied without losing performance.

Example 2 (According to the Invention)

The metal chlorides are impregnated on an alumina support from Sasol with the labelling Catalox SCCa 25/200. The metal composition is 4.3 wt. % Cu, 1.3 wt. % Mg, 1.0 wt. % Mn.

Example 3 (According to the Invention)

The metal chlorides are impregnated on an alumina support from Sasol with the labelling Catalox SCCa 25/200. The metal composition is 4.3 wt.-% Cu, 1.3 wt.-% Mg, 0.4 wt.-% K, 1.5 wt.-% Mn.

Comparative Example 4a (According to EP 375202)

The metal chlorides are impregnated on an alumina support from Sasol with the labelling Catalox SCCa 25/200. The metal composition is 4.3 wt. % Cu, 1.3 wt. % Mg, 1.1 wt. % K.

Comparative Example 4b (According to EP 375202)

The metal chlorides are impregnated on an alumina support from Sasol with the labelling Puralox SCCa 25/200. The metal composition is 4.3 wt. % Cu, 1.3 wt. % Mg, 1.1 wt. % K.

Comparative Example 5 (According to Example 3 in DD 90127)

The metal chlorides were impregnated on an alumina support from Sasol with the labelling Catalox SCCa 25/200. The metal composition is 4.3 wt. % Cu, 1.2 wt. % K, 1.0 wt. % Mn.

Comparative Example 6 (According to EP 0582165)

The metal chlorides are impregnated on an alumina support from Sasol with the labelling Catalox SCCa 25/200 (This support has a pore volume of 0.43 mL/g and a surface area of 200 m$^2$/g. The psd of the alumina is such that 1.6% of the particles is smaller than 22 μm, 8.8% of the particles is smaller than 31 μm, 28.5% of the particles is smaller than 44 μm, 84.7% of the particles is smaller than 88 μm and 98.1% of the particles is smaller than 125 μm.). The metal composition is 4.3 wt. % Cu, 1.3 wt. % Mg, 1.1 wt. % K, 2.5 wt. % Rare Earths (60% La, 20% Ce, 20% Pr). The impregnation is carried out in a V-blender at 60-75° C., the volume of the impregnation solution is 90%±5% of the pore volume of the alumina support. The drying is carried out in a dryer that is operated between 100-140° C.

Results

Comparison of the chemical performance of examples 1a, 1c and comp. example 5 in test reactor 2

| | HCl conversion (%) | Ethylene conversion (%) | EDC selectivity (%) | CO$_x$ selectivity (%) | Cl-by-product selectivity (%) |
|---|---|---|---|---|---|
| 240° C. | | | | | |
| Example 1a | 99.8 | 97.7 | 95.6 | 3.7 | 0.73 |
| Example 1c | 99.8 | 97.8 | 95.5 | 3.7 | 0.89 |
| Comp. ex. 5 | 99.5 | 98.6 | 93.9 | 5.1 | 0.95 |
| 235° C. | | | | | |
| Example 1a | 99.8 | 96.9 | 96.7 | 2.7 | 0.57 |
| Example 1c | 99.8 | 97.0 | 96.6 | 2.7 | 0.72 |
| Comp. ex. 5 | 99.6 | 97.8 | 95.2 | 4.1 | 0.76 |
| 230° C. | | | | | |
| Example 1a | 99.7 | 96.2 | 97.6 | 1.9 | 0.48 |
| Example 1c | 99.7 | 96.3 | 97.5 | 1.9 | 0.57 |
| Comp. ex. 5 | 99.5 | 96.9 | 96.5 | 2.9 | 0.61 |

The tests show that the catalysts according to the invention are superior in both HCl conversion and EDC selectivity compared to the prior art catalyst described in DD 90127.

Comparison of example 1a and comparative example 4a in test reactor 1.

| Reaction temperature (° C.) | HCl conversion (%) example 1a | HCl conversion (%) comp. ex. 4a | EDC selectivity (%) example 1a | EDC selectivity (%) comp. ex. 4a |
|---|---|---|---|---|
| 230 | 99.6 | 99.4 | 94.9 | 94.6 |
| 225 | 99.6 | 99.4 | 95.8 | 96.1 |
| 220 | 99.6 | 99.3 | 97.3 | 97.3 |
| 215 | 99.5 | 98.9 | 98.1 | 98.4 |
| 210 | 98.8 | sticking | 98.9 | sticking |

At a given temperature the HCl conversion of the inventive example is higher than for the comparative example. The EDC selectivity is similar. Hence at a same HCl conversion the inventive catalyst shows a higher EDC selectivity than the comparative example. Furthermore the comparative example is more sensitive to stickiness. While the inventive catalyst can still be operated far below 210° C., the comparative example started to stick up when the reaction temperature was brought down to 210° C.

Comparison of example 1b and comparative example 4b in test reactor 2

| Reaction temperature (° C.) | HCl conversion (%) example 1b | HCl conversion (%) comp. ex. 4b | EDC selectivity (%) example 1b | EDC selectivity (%) comp. ex. 4b |
|---|---|---|---|---|
| 240 | 99.9 | 99.8 | 94.7 | 95.9 |
| 235 | 99.9 | 99.8 | 96.2 | 97.0 |
| 230 | 99.9 | 99.7 | 97.2 | 98.0 |
| 225 | 99.8 | 99.4 | 98.0 | 98.7 |
| 219 | 98.9 | sticking | 98.6 | sticking |

At a given temperature the HCl conversion of the inventive example is higher and the EDC selectivity is lower than for the comparative example. However, in oxychlorination selectivities should not be compared at a same temperature but at a same HCl conversion as a minimum HCl conversion of 99.5-99.6% is required. At a same HCl conversion the inventive catalyst shows higher EDC selectivities than the comparative example. Furthermore the comparative example is more sensitive to stickiness. While the inventive catalyst can still be operated at 219° C., the comparative example started to stick up when the reaction temperature was brought down to 220° C.

Comparison of examples 2 and 3 and comparative example 5 in test reactor 2

| Reaction temperature (° C.) | example 2 | example 3 | comp. ex. 5 | example 2 | example 3 | Comp. ex. 5 |
|---|---|---|---|---|---|---|
| | HCl conversion (%) | | | EDC selectivity (%) | | |
| 230 | 99.8 | 99.8 | 99.5 | 95.8 | 96.5 | 96.5 |
| 225 | 99.8 | 99.7* | 99.4 | 96.9 | 97.8* | 97.4 |
| 220 | 99.7 | n.d. | 98.9 | 98.0 | n.d. | 97.7 |
| 217.5 | 99.8 | 99.3** | 98.5 | 98.5 | 98.6** | 98.1 |
| | Cl-by-product selectivity (%) | | | CO$_x$ selectivity (%) | | |
| 230 | 0.54 | 0.5 | 0.63 | 3.7 | 3.0 | 2.9 |
| 225 | 0.46 | 0.47* | 0.61 | 2.6 | 1.8* | 2.0 |
| 220 | 0.43 | n.d. | 0.68 | 1.6 | n.d. | 1.4 |
| 217.5 | 0.52 | 0.5 | 0.76 | 1.0 | 0.9 | 1.1 | n.d.: not determined
*Reaction temperature: 224° C.
**Reaction temperature: 218° C.

Examples 2 and 3 are catalysts designed to be operated at lower temperatures. The results show that they can be operated as low as 217.5° C. without losing HCl conversion. Comparison example 5 has an inferior HCl conversion over the whole temperature range. Furthermore the EDC selectivities of example 2 and example 3 are better at lower temperatures compared to comparative example 5, although they have higher HCl conversions. Especially the formation of chlorinated by-products is lowered with regard to the comparative example.

The following Table summarizes the impact of replacing the rare earth additives with Mn. Each formulation contains the same mass % of Cu, K, and Mg. An equivalent Mn to total rare earth molar concentration per kg of catalyst was used when comparing the Mn to the rare earth formulation. As the results indicate the replacement of the rare earth additives in a Cu, Mg, K, rare earth formulation generates a catalyst formulation that is more resistant to process upsets that lead to catalyst stickiness. Low operating temperature and or high partial HCl pressure due to low HCl conversion are typical process upsets that can lead to a fluidization failure due to the onset of catalyst stickiness. As the results indicate, surprisingly, the Mn formulation is much more resistant to becoming sticky under the conditions of low operating temperature and low HCl conversion when compared to the Rare Earth formulation. A 50/50 physical mixture by weight of the rare earth formulation (comparative Ex. 6) and the Mn formulation (inventive Ex. 1c) fails at a point intermediate to formulations containing only Mn in addition to Cu, Mg, and K, or only rare earth additives, in addition to Cu, Mg, and K, thus confirming the observation that Mn improves the operability or resistance to stickiness of prior art formulations.

The comparative stickiness tests were completed in test reactor 1 by lowering the reactor operating temperature by 2 to 3° C. after it was confirmed that stickiness onset had not occurred at the previous operating temperature following 48 Hr of operation. The temperature and HCl conversions resulting in fluidization failure due to stickiness upsets indicate the advantage of the Mn formulation. After 72 hours at 198° C. the test was terminated for the Mn formulation due to its superior resistance to stickiness relative to the comparative formulations.

| Formulation | Temperature (° C.) | HCl Conversion (%) | Differential Pressure Reading | Visual Observation |
|---|---|---|---|---|
| Cu/K/Mg (Comp. Ex. 4a) | 210 | 98.1 | "high noise" | slugging |
| Cu/K/Mg/La/Ce/Pr (Comp. Ex. 6) | 205 | 94.4 | "high noise" | slugging |
| Cu/K/Mg/La/Ce/Pr/Mn (50/50 wt % Ex. 6 and Ex. 1c) | 205 | 95.2 | "low noise" | fluid |
| Cu/K/Mg/La/Ce/Pr/Mn (50/50 wt % Ex. 6 and Ex. 1c) | 202 | 92.3 | "high noise" | slugging |
| Cu/K/Mg/Mn (Inventive Ex. 1c) | 200 | 90.8 | "low noise" | fluid |
| Cu/K/Mg/Mn (Inventive Ex. 1c) | 198 | 87.1 | "low noise" | fluid |

Certain embodiments of the invention are envisioned where at least some percentages, temperatures, times, and ranges of other values are preceded by the modifier "about." "Comprising" is intended to provide support for "consisting of" and "consisting essentially of." Where ranges in the claims of this application do not find explicit support in the specification, it is intended that such claims provide their own disclosure as support for claims or teachings in this or a later filed application. Numerical ranges of ingredients that are bounded by zero on the lower end (for example, 0-2 wt. % K) are intended to provide support for the concept "up to [the upper limit]," for example "up to 2 wt. % K," vice versa, as well as a positive recitation that the ingredient in question is present in an amount that does not exceed the upper limit. An example of the latter is "comprises K, provided the amount does not exceed 2 wt. %."

While the invention herein disclosed has been described by means of specific embodiments and applications thereof, numerous modifications and variations could be made thereto by those skilled in the art without departing from the scope of the invention set forth in the claims. Furthermore, various aspects of the invention may be used in other applications than those for which they were specifically described herein.

What is claimed is:

1. A process for preparing a catalyst composition, the process comprising:
   wetting a high surface area support material with an aqueous solution, the aqueous solution comprising:
   a copper salt;
   one or more alkali metal salts;
   one or more alkaline earth metal salts; and
   one or more further transition metal salts comprising Mn or Re salts, or mixtures thereof; and
   drying the wetted high surface area support material,
   the high surface area support material having a BET surface area of from about 80 to about 220 m$^2$/g;
   wherein the aqueous solution is free of rare earth metals; and wherein the prepared catalyst composition comprises:
   from about 2 to about 8% by weight of copper as metal,
   from about 0.1 to about 0.6 moles/kg of one or more alkali metals as metal,
   from about 0.08 to about 0.85 moles/kg of one or more alkaline earth metals as metal, and from about 0.09 to about 0.9 moles/kg of the one or more Mn or Re metals as metal;

wherein amounts of the metals are based on a total weight of the catalyst composition, and wherein the catalyst composition is free of rare earth metals.

2. The process of claim 1, wherein the high surface area support comprises silica, magnesia, kieselguhr, clay, fuller's earth, alumina, or combinations thereof.

3. The process of claim 2, wherein the high surface area support comprises fluidizable alumina.

4. The process of claim 2, wherein the high surface area support comprises multiple mixed phases of alumina comprising gamma alumina, delta alumina, theta-alumina, or combinations thereof.

5. The process of claim 1, wherein the one or more alkali metals comprise potassium.

6. The process of claim 4, wherein the high surface area support material comprises stabilizing components.

7. The process of claim 6, wherein the stabilizing components comprise Ti, or Si.

8. The process of claim 4, wherein the high surface area support material comprises impurities.

9. The process of claim 8, wherein the impurities comprise metal oxides comprising sodium oxide, iron oxide, titanium dioxide, iron oxide, or silicon dioxide.

10. The process of claim 1, wherein the prepared catalyst composition comprises:
    about 3% to about 6% by weight copper as metal,
    about 0.1 to about 0.4 moles/kg one or more alkali metals as metal,
    about 0.2 to about 0.75 moles/kg one or more alkali earth metals as metal, and
    about 0.09 to about 0.4 moles/kg Mn or Re metals as metal.

11. The process of claim 1, wherein the prepared catalyst composition comprises:
    about 2 to about 8% by weight copper as metal,
    about 0.1 to about 2% by weight potassium as metal,
    about 0.2 to about 2.0% by weight magnesium as metal, and
    about 0.5 to about 5.0% by weight manganese as metal.

12. The process of claim 1, wherein the one or more alkali metal salts comprises a chloride or carbonate salts of at least one metal selected from the group consisting of potassium, lithium, sodium, rubidium, and cesium.

13. The process of claim 1, wherein the one or more alkaline earth metal salts comprises a chloride or carbonate salt of magnesium.

14. The process of claim 1, wherein the one or more transition metal salts comprises a chloride or carbonate salt of manganese.

15. The process of claim 1, wherein the one or more alkali metals comprise potassium, the one or more alkaline earth metals comprise magnesium, and the one or more further transition metals comprise manganese.

16. The process of claim 1, wherein the catalyst composition does not stick or agglomerate during an oxychlorination process at a temperature ranging from about 180° C. to about 260° C.

* * * * *